United States Patent
Loboda

(10) Patent No.: US 7,459,679 B2
(45) Date of Patent: Dec. 2, 2008

(54) METHOD AND APPARATUS FOR MASS SELECTIVE AXIAL TRANSPORT USING PULSED AXIAL FIELD

(75) Inventor: Alexander Loboda, Ontario (CA)

(73) Assignees: MDS Inc. CT (US); Applera Corporation, Concord (CA)

( * ) Notice: Subject to any disclaimer, the term of this patent is extended or adjusted under 35 U.S.C. 154(b) by 240 days.

(21) Appl. No.: 11/558,952

(22) Filed: Nov. 13, 2006

(65) Prior Publication Data

US 2007/0120053 A1 May 31, 2007

Related U.S. Application Data

(60) Provisional application No. 60/740,640, filed on Nov. 30, 2005.

(51) Int. Cl.
*H01J 49/42* (2006.01)
*B01D 59/44* (2006.01)

(52) U.S. Cl. .................................................... 250/292

(58) Field of Classification Search ................. 250/281, 250/282, 290, 292, 293, 286, 287
See application file for complete search history.

(56) References Cited

U.S. PATENT DOCUMENTS

| 5,847,386 | A | 12/1998 | Thomson et al. |
| 6,177,668 | B1 | 1/2001 | Hager |
| 6,504,148 | B1 | 1/2003 | Hager |
| 6,630,662 | B1 | 10/2003 | Loboda |
| 2005/0253064 | A1* | 11/2005 | Loboda et al. ............... 250/292 |

OTHER PUBLICATIONS

Londry & Hager, "Mass Selective Axial Ejection from a Linear Quadrupole Ion Trap", J Am Soc Mass Spectrom, 2003, 14, 1130-1147.
Loboda, A., Krutchinsky A., Loboda, O. , McNabb, J., Spicer, V., Ens W., Standing, K. Eur. J. Mass Spectrom. 2000. 6: 531-536.
Written Opinion of the International Searching Authority for application No. PCT/CA2006/001692, p. 1-4.
International Search Report for application No. PCT/CA2006/001692, p. 1-3.

* cited by examiner

*Primary Examiner*—Jack I Berman
*Assistant Examiner*—Michael Maskell
(74) *Attorney, Agent, or Firm*—Bereskin & Parr

(57) ABSTRACT

A mass spectrometer system has an elongated rod set having an entrance end, an exit end, a plurality of rods and a central longitudinal axis. The mass spectrometer system is operable to perform the following steps: a) admitting a first plurality of groups of ions into the entrance end of the rod set; b) producing a field between the plurality of rods to confine the first plurality of groups of ions in the rod set; c) selecting a first mass/charge range for a first group of ions in the first plurality of groups of ions; d) providing a first radial excitement field to radially displace the first group of ions within the first mass/charge range from the central longitudinal axis, and concurrently retaining a second group of ions closer to the central longitudinal axis than the first group of ions, the second group of ions being within a second mass/charge range disjoint from the first mass/charge range; and then e) providing a first axial force acting on the first group of ions by providing an axial acceleration field. The first axial force is not provided during step d).

22 Claims, 11 Drawing Sheets

METHOD AND APPARATUS FOR MASS SELECTIVE AXIAL TRANSPORT USING PULSED AXIAL FIELD

RELATED APPLICATIONS

The application claims the benefit of U.S. Provisional Application Ser. No. 60/740,640, filed Nov. 30, 2005, the entire contents of which is hereby incorporated by reference.

FIELD

The present invention relates generally to mass spectrometry, and more particularly relates to a method and apparatus for selective axial transport using pulsed axial field.

INTRODUCTION

Many types of mass spectrometers are known, and are widely used for trace analysis to determine the structure of ions. These spectrometers typically separate ions based on the mass-to-charge ratio ("m/z") of the ions. One such mass spectrometer system involves mass-selective axial ejection—see, for example, U.S. Pat. No. 6,177,668 (Hager), issued Jan. 23, 2001. This patent describes a linear ion trap including an elongated rod set in which ions of a selected mass-to-charge ratio are trapped. These trapped ions may be ejected axially in a mass selective way as described by Londry and Hager in "*Mass Selective Axial Ejection from a Linear Quadrupole Ion Trap*," J Am Soc Mass Spectrom 2003, 14, 1130-1147. In mass selective axial ejection, as well as in other types of mass spectrometry systems, it will sometimes be advantageous to control the axial location of different ions.

SUMMARY

In accordance with an aspect of a first embodiment of the invention, there is provided a method of operating a mass spectrometer system. The mass spectrometer system has an elongated rod set having an entrance end, an exit end, a plurality of rods and a central longitudinal axis. The method comprises: a) admitting a first plurality of groups of ions into the entrance end of the rod set; b) producing a field between the plurality of rods to confine the first plurality of groups of ions in the rod set; c) selecting a first mass/charge range for a first group of ions in the first plurality of groups of ions; d) providing a first radial excitement field to radially displace the first group of ions within the first mass/charge range from the central longitudinal axis, and concurrently retaining a second group of ions closer to the central longitudinal axis than the first group of ions, the second group of ions being within a second mass/charge range disjoint from the first mass/charge range; and then e) providing a first axial force acting on the first group of ions by providing an axial acceleration field. The first axial force is not provided during step d).

In accordance with an aspect of a second embodiment of the invention, there is provided a mass spectrometer system comprising: a) an ion source; b) a rod set, the rod set having a plurality of rods extending along a longitudinal axis, an entrance end for admitting ions from the ion source, and an exit end for ejecting ions traversing the longitudinal axis of the rod set; c) a voltage supply module for producing an RF field between the plurality of rods of the rod set; and, d) a controller for controlling the voltage supply module to provide a radial excitement field to, i) during an excitation phase of operation, radially displace a first group of ions within a selected mass/charge range from the central longitudinal axis, and concurrently retain a second group of ions closer to the central longitudinal axis than the first group of ions, the second group of ions being within a second mass/charge range disjoint from the selected mass/charge range; and then ii) during an axial acceleration phase of operation, provide an axial force acting on the first group of ions by providing an axial acceleration field. The controller is further operable to control the voltage supply module to interrupt the axial acceleration field during the excitation phase of operation such that the derived axial force is not provided during the excitation phase of operation.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicants' teachings in anyway.

DESCRIPTION OF VARIOUS EMBODIMENTS

Figure 1:
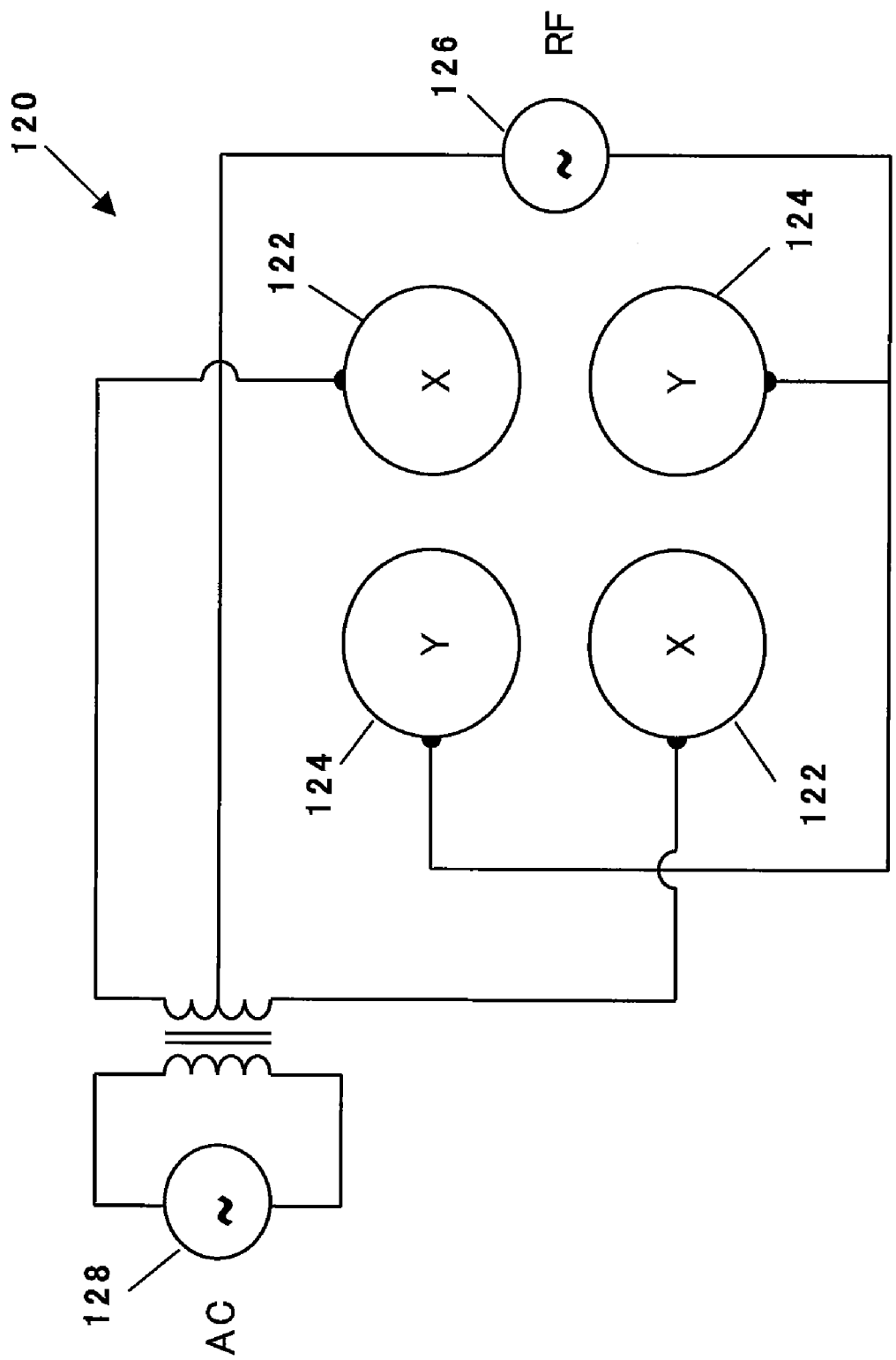
FIG. 1, in a schematic view, illustrates a quadrupole rod set in which a dipolar auxiliary signal is provided to one of the rod pairs.

Referring to FIG. 1, there is illustrated in a schematic view a quadrupole rod set 120 in which a dipolar auxiliary AC signal can be provided to one of the rod pairs. Specifically, the quadrupole rod set 120 comprises a pair of X-rods 122 and a pair of Y-rods 124 to which RF voltage can be applied (in a known manner) by RF voltage source 126 to provide radial confinement of ions. The exit end of the quadrupole rod set 120 can be blocked by supplying an appropriate voltage to an exit electrode at the exit end.

In addition to the RF voltage that can be applied to all of the rods by RF voltage source 126, an auxiliary dipolar signal can be provided to X-rods 122 without being provided to Y-rods 124, by AC voltage source 128 (in a known manner).

According to some aspects of the invention, the RF voltage supplied to the X-rods and Y-rods comprises a quadrupolar DC component. The quadrupolar DC component applied to the X-rods is opposite in polarity to the quadrupolar DC component applied to the Y-rods. As will be described in more detail below in connection with FIGS. 2 to 7, the quadrupolar DC applied to the X-rods and Y-rods is applied in such a way that its magnitude may be varied along the lengths of the rods. At other times, the quadrupolar DC applied to the X-rods and the Y-rods may be kept constant along the length of the rods.

Specifically, according to some aspects of the present invention, illustrated in Figure and described below, the quadrupolar DC profile provided along one pair of rods in the rod set diminishes linearly from a maximum at the entrance end of the rod set to a minimum at the exit end of the rod set, while the quadrupolar DC profile applied to the other pair of rods in the rod set increases linearly from a minimum at the entrance end of the rod set to a maximum at the exit end of the rod set. In these aspects of the invention, the quadrupolar DC components applied to both pairs of rods of the quadrupolar rod set can be made constant along the length of the rod set by simply making both of these quadrupolar DC voltages equal to zero.

According to other aspects of the invention described below in connection with FIGS. 4 to 7, segmented rod sets are provided. In the case of some of these segmented rod sets, the quadrupolar DC voltages applied to the rod sets may be made uniform along the length of the rods without necessarily being zero.

The derived axial force resulting from a linear variation in the DC quadrupolar voltage applied to the rods can be calculated, for the two-dimensional mid-section of a linear quadrupole rod set, by considering the contribution to the potential of the quadrupolar DC. In the central portion of a linear ion trap where end effects are negligible, the two-dimensional quadrupole potential can be written as $$Ö_{2D} = \varphi_0 \frac{x^2 - y^2}{r_0^2} \quad (1)$$

where $2r_0$ is the shortest distance between opposing rods and $\phi_0$ is the electric potential, measured with respect to ground, applied with opposite polarity to each of the two poles. Traditionally, $\phi_0$ has been written as a linear combination of DC and RF components as $$\phi_0 = U - V\cos\Omega t \quad (2)$$

where U is the angular frequency of the RF drive.

In this instance, we may disregard the alternating RF term and write the DC contribution as a linear function of the axial coordinate z, measured from the axial position at which the quadrupolar DC is a maximum, as $$Ö_{DC} = U_0\left(1 - \frac{z}{z_0}\right)\frac{x^2 - y^2}{r_0^2} \quad (3)$$

where, $U_0$ is the level of the quadrupolar DC applied to the entrance end of the rods and $z_0$ is the axial dimension over which the quadrupolar DC is applied. The axial component of the electric field can be obtained by differentiating Eq. 3 with respect to the axial coordinate z to yield the following:

$$E_z = \frac{U_0}{z_0 r_0^2}(x^2 - y^2) \quad (4)$$

Consideration of Eq. 4 yields three significant features. First, the force is axially uniform (provided, of course, that the DC quadrupolar voltage varies linearly along the length of the rods). Second, axial field strength depends quadratically on radial displacement. Finally, the sign of the derived axial force is positive in the x–z plane but negative in the y–z plane.

To facilitate discussion, assume that the ions are positive and the polarity of the quadrupole DC applied to the X-pole rods is also positive. The discussion would apply equally well if the polarity of the ions was negative and the polarity of the quadrupolar DC applied to the X-pole rods was negative.

Figure 2:
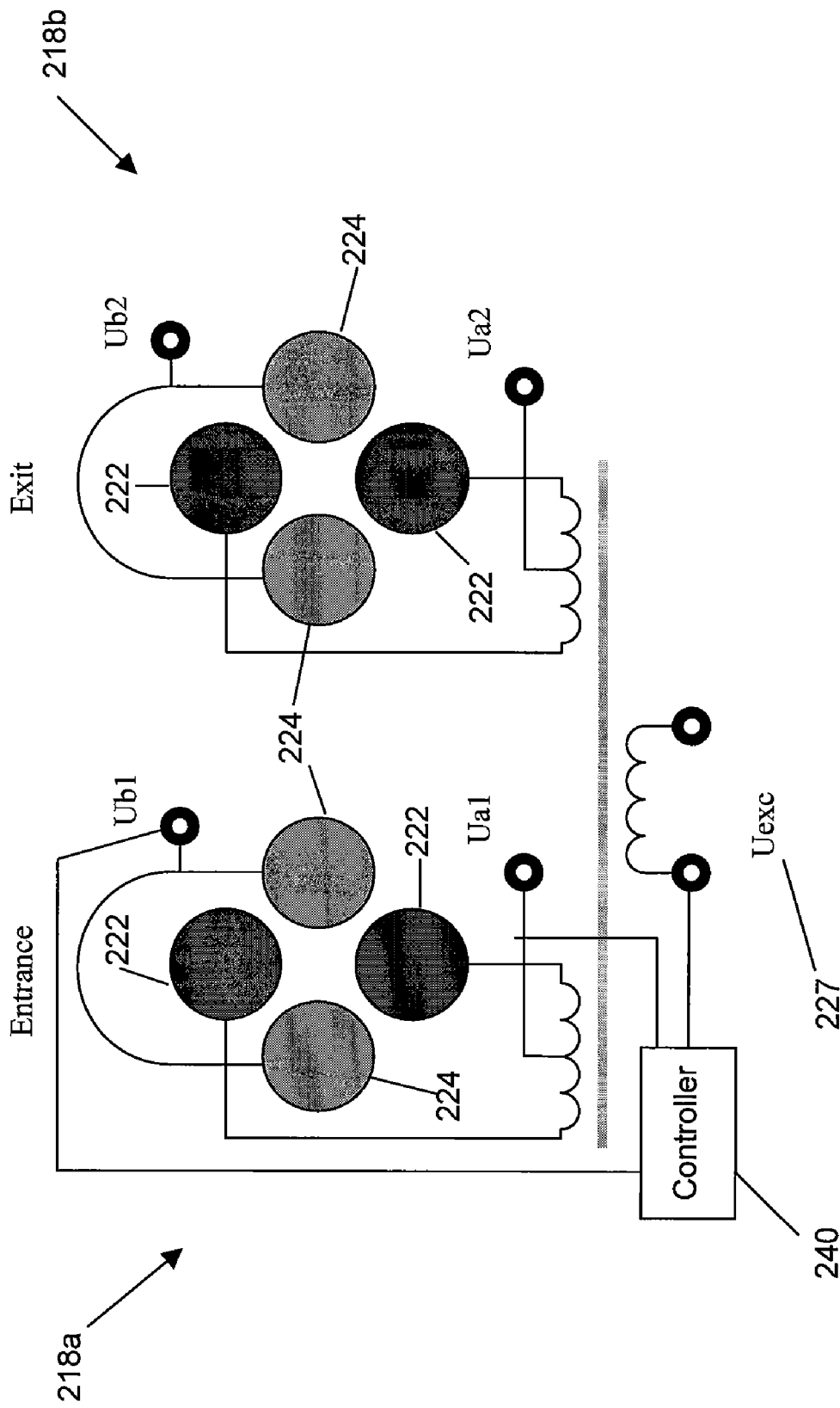
FIG. 2, in a schematic view, illustrates the ends of an ion guide in accordance with a first aspect of the present invention.

Referring to FIG. 2 there is illustrated in a schematic diagram, an ion guide 218 in accordance with a first aspect of the present invention. For brevity, the description of FIG. 1 will not be repeated with respect to FIG. 2. Instead, and for clarity, elements analogous to those described above in connection with FIG. 1 will be designated using the same reference numerals, plus 100.

As shown in FIG. 2, a quadrupolar DC voltage Ua1 can be applied to the X-rods 222 at an entrance end 218a of the ion guide 218, and a exit quadrupolar DC voltage Ua2 can be supplied to the X-rods 222 at an exit end 218b of the ion guide 218. Similarly, an entrance quadrupolar DC voltage Ub1 can be supplied to the Y-rods 224 at the entrance end 218a of the ion guide 218, while an exit quadrupolar DC voltage Ub2 can be supplied to the Y-rods 224 at the exit end 218b of the ion guide 218. Quadrupolar DC voltages Ua1, Ua2, Ub1 and Ub2 are all controlled by a controller 240.

In FIG. 2, entrance electrode S1 and exit electrode S2 are not shown. Electrodes S1 and S2 can be used to provide entrance and exit barriers. As will be described below in more detail, the four-quadrupolar rods may be made as segmented rods, or employ a semiconductive coat to provide a linear voltage gradient along the axis. During an axial acceleration mode, the axial field created by one pair of rods cancels the field created by the other pair of rods such that ions that are near the axis do not encounter significant force pushing them in the axial direction. However, ions that have been excited such that they are closer to one of the pairs of rods than to the other pair of rods will encounter a field pushing them axially in one direction and will accordingly be accelerated. Once these excited ions pick up enough energy in the longitudinal direction, the axial acceleration mode can be turned off. Then, a small voltage on the exit barrier S2 at the exit end 218b of the ion guide 218 can be used to keep all of the ions in the trap except for the ions accelerated toward the exit end 218b.

The above-described method of pulsing an axial acceleration field for selective axial mass transport involves the following steps. In the first step, multiple precursor ions of interest can be trapped and isolated. In this step, Ua1 can equal Ua2 and Ub1 can equal Ub2 such that no axial acceleration field is provided. In some embodiments, Ua1=Ua2=Ub1=Ub2. Similarly, S1 and S2 can be, and in some embodiments are, greater than Ua1 to prevent ions from escaping from either the entrance end 218a or the exit end 218b of the ion guide. In this step, either filtered noise fields (FNF) or stored waveform inverse fourier transforms (SWIFT) can be used to isolate precursor ions of interest.

Alternatively, precursor ions of interest can be filtered using low and high mass filtering by changing the RF and DC (such that Ua1=Ua2≠Ub1=Ub2).

In step 2, the precursor ion with the lowest mass-to-charge (m/z) can be excited using dipolar excitement voltage 227, which is also controlled by controller 240. Again, during this step of radially exciting a selected ion of interest, Ua1=Ub1 and Ua2=Ub2. Similarly, S1 and S2 are both greater than Ua1 in order to longitudinally contain the ions.

In step 3, an axial acceleration mode is used to accelerate the ions excited in step 2 toward the exit end 218b of the ion guide 218. As discussed above, in this step Ua1 is not equal to Ua2, and Ub1 is not equal to Ub2 such that the non-zero quadrupolar DC voltage gradient along the ion guide 218 gives rise to a derived axial force (according to equation 4) that acts on ions that are radially displaced from the central axis. Since ions are oscillating around the axis the average axial field acting on ions can be expressed as:

$$E_z^{avr}(z) = \frac{U_z}{z_0} * \frac{x_0^2}{2r^2} \quad (4a)$$

where $E_z^{avr}$ is the average axial force and $x_0$ is the excitation amplitude. According to some aspects of the invention, Ua1=Ub2 and Ub1=Ua2. For example, Ua1 and Ub2 may both be positive 5 Volts, while Ub1 and Ua2 are both negative 5 Volts. This voltage configuration can be desirable as it keeps the DC voltages low which is advantageous for extending the mass range of ions stored in the trap. In this axial acceleration step, S1 and S2 remain greater than Ua1, as it is still important to keep the ions axially trapped within the ion guide 218. Further, this axial acceleration step must continue for sufficient time for the excited ions to acquire sufficient axial energy to get past S2 in step 4. Assuming excited ions have negligible velocity in the axial direction when the acceleration field is switched on, the axial velocity after time interval T will be $$v_z = \frac{1}{m/q} \frac{U_z}{z_0} * \frac{x_0^2}{2r^2} * T \quad (5)$$

and, the energy of the ion in the axial direction will be $$W_z = \frac{mv_z^2}{2} \quad (6)$$
$$= \frac{m}{2}\left(\frac{1}{m/q} \frac{U_z}{z_0} * \frac{x_0^2}{2R^2} * T\right)^2.$$

In step 4, the axial acceleration field is turned off. That is, Ua1=Ua2 and Ub1=Ub2. After this axial acceleration mode is ended, the voltage S2 applied to the exit electrode can be dropped to be, for example, just above 0.5*(Ua1+Ub1) to let excited ions get past the exit electrode and out of the trap, while retaining the other ions.

Subsequent to axial ejection step 4, steps 2 to 4 can be repeated for other precursor ions of interest isolated in step 1. To excite these precursor ions of successively higher mass into resonance with the dipolar auxiliary signal of the same frequency provided in step 2, the amplitude of the RF voltage can be increased. Alternatively, the RF voltage amplitude can be maintained while the frequency of the auxiliary signal can be readjusted to coincide with the frequency of motion of each new precursor ion of interest. After all of the ions initially selected in step 1 have been processed, steps 1 to 5 can be repeated using a new group of ions. Optionally, the ions may be mass selectively ejected in different orders. For example, in step 2 the precursor ion with the highest m/z could be excited using dipolar excitement voltage 227, and subsequently ejected using steps 3 and 4. Then, the amplitude of the RF voltage could be successively decreased to bring ions of lower mass into resonance with the low-amplitude dipolar auxiliary signal. Alternatively, the RF voltage can be both increased and decreased during a cycle to excite ions of different m/z in different orders.

Figure 3:
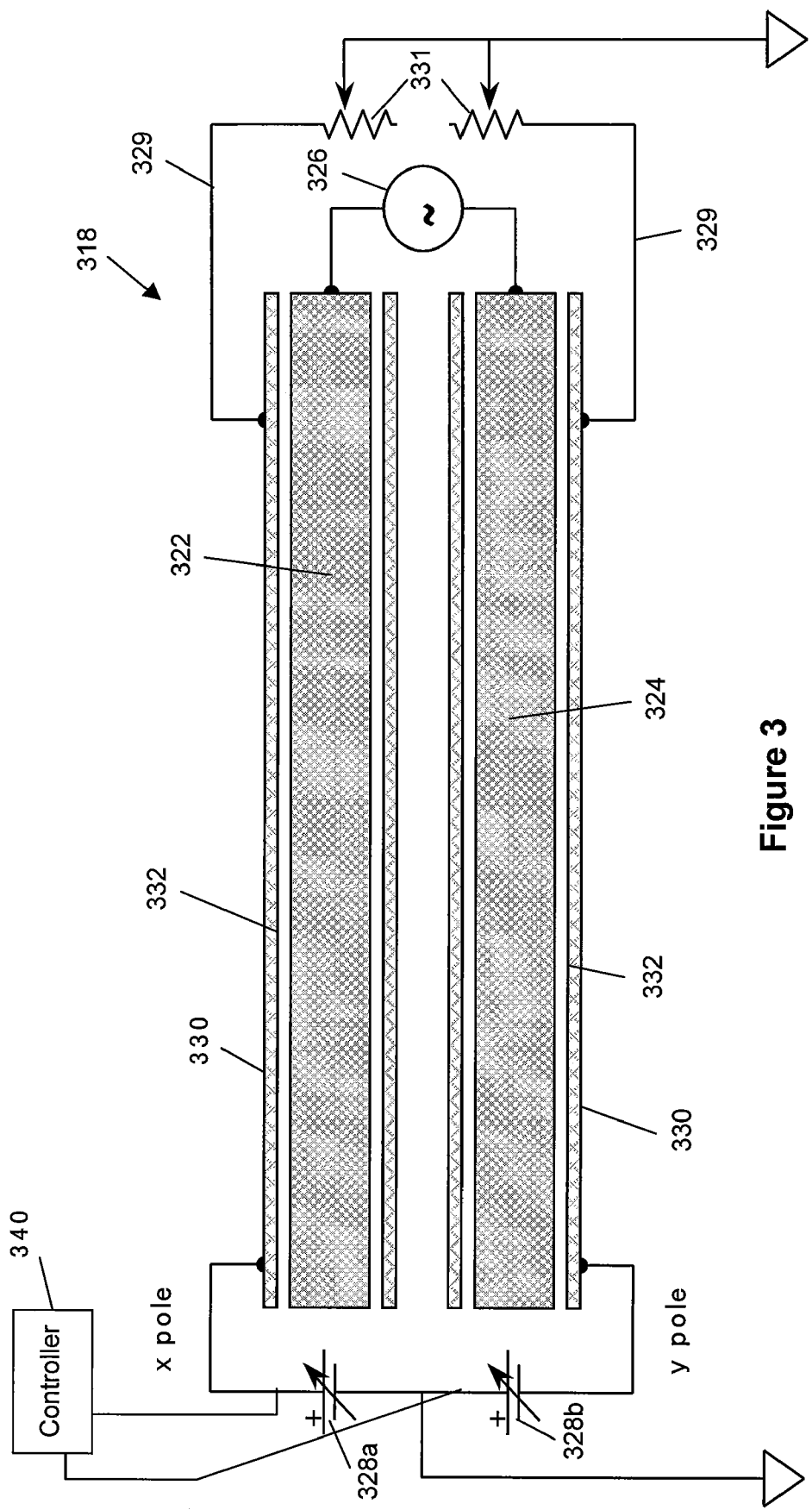
FIG. 3, in a schematic view, illustrates an ion guide in accordance with a second aspect of the present invention.

Referring to FIG. 3, there is illustrated in a schematic diagram, an ion guide 318 in accordance with a further aspect of the invention. For brevity, the description of FIG. 2 is not repeated with respect to FIG. 3. For clarity, elements analogous to those described above in connection with FIG. 2 will be designated using the same reference numerals, with 100 added.

As shown in FIG. 3, both the X-rods 322 and Y-rods 324 can be coated with a high-dielectric insulating layer 332. In some embodiments, this insulating layer 332 is capable of isolating a minimum of 10 Volts DC. This insulating layer 332 can, in turn, coated with a thin resistive coating 330. In some embodiments, this thin resistive coating 330 offers an end-to-end resistance on each rod of 1 Ω to 100 MΩ. Preferably, both the resistive coating 330 and insulating layer 332 should be as thin as possible.

As shown in FIG. 3, quadrupolar DC can be applied at one end of the X-rods 322 and Y-rods 324 by variable DC quadrupolar voltage sources 328a and 328b respectively. The DC quadrupolar voltages provided by variable DC quadrupolar voltage sources 328a and 328b are opposite in polarity. Variable DC quadrupolar voltage sources 328a and 328b can be controlled as described below by a controller 340. Controller 340 can also controllably add a dipolar excitation voltage to at least one of the X-rods 322 and Y-rods 324. The ground connection for the sources 328a and 328b and to potentiometers 331 can be superimposed onto the RF voltage supplied by RF supply 326. Even though this arrangement is more complicated from an electrical point of view it relaxes the requirements for the insulating layer 332 since there will be no RF potential difference between the rods 322, 324 and the conductive coating 330. An additional advantage of this configuration is that the conductive coating can have lower resistance, down to 1 Ohm, since there is no need to decouple the RF and DC voltages supplied to the conductive coating.

In accordance with an aspect of the present invention, the ion guide 318 of FIG. 3 can be used for mass selective axial transport using pulsed quadrupolar DC. To begin with, a first plurality of groups of ions would be admitted into the entrance end of the ion guide 318, each group of ions in this plurality of group of ions having a different m/z. An RF confinement field could be provided in a known manner between the X-rods 322 and Y-rods 324 to radially confine this first plurality of groups of ions in the rod set. A user/operator can then select a first mass/charge ratio (m/z) for a first group of ions in the first plurality of groups of ions. The user can then operate the controller 340 to provide a first radial excitation field using a dipolar excitation voltage. This first radial excitation field displaces the first group of ions, which have the first selected mass/charge range, from the central longitudinal axis. Concurrently, a second group of ions, which has a second mass/charge range disjoint from the first selected mass/charge range is retained closer to the central longitudinal axis of the ion guide 318 than the excited first group of ions. This can be done by selecting a first RF amplitude of the RF field to bring the first group of ions into resonance with the dipolar electrical signal.

After the first group of ions have been radially excited, an axial acceleration field is provided to provide a first axial force acting on the first group of ions. The axial acceleration field can be provided, and in some embodiments is provided, by providing a first quadrupolar DC voltage to the X-rods 322 and a second quadrupolar DC voltage to the Y-rods 324 using DC quadrupolar voltage sources 328a and 328b respectively. The first quadrupolar DC voltage is opposite in polarity to the second quadrupolar DC voltage. Both the first and second quadrupolar DC voltages are provided to the resistive coating 330. The end-to-end resistance of the resistive coating 330 results in a drop in potential in both the first quadrupolar DC voltage and the second quadrupolar DC voltage along the length of the X-rods 322 and Y-rods 324. As a result, the axial acceleration field provided by the first quadrupolar DC voltage and the second quadrupolar voltage is generated along the length of the rod set. This, as described above, provides the first axial force that acts on the first group of ions. Optionally, the resistive coating 330 may be provided along only a portion of the rods such that the axial acceleration field varies along only this portion of the length of the rod set. Assuming the resistance of the resistive coating 330 is substantially uniform, the first and second quadrupolar DC voltages will vary linearly along the length of the ion guide 318, creating a constant axial force that acts on the first group of ions.

As described above, the axial acceleration field is maintained for long enough to impart sufficient momentum to the first group of ions to axially eject this first group of ions past an exit barrier field provided at the exit end of the ion guide 318. At the same time, the exit barrier field is sufficient to impede axial ejection of the second group of ions from the exit end.

In some embodiments, the axial acceleration field is not provided at the same time as the radial excitement field, as the axial acceleration field may skew the effect of the radial excitement field, such that ions of slightly differing m/z are radially excited at different points along the length of the ion guide 318. Thus, while the first group of ions is being radially excited within ion guide 318, the first and second quadrupolar DC voltages can be eliminated, such that no quadrupolar DC gradient is provided along the lengths of the ion guide 318. As a result, the axial force derived from this axial acceleration field would not be provided during radial excitement of the first group of ions. In some embodiments, the radial excitement field would also be interrupted while the axial acceleration field would be provided. This could be done by simply interrupting the dipolar excitement voltage.

Rod sets as described in FIG. 3 may be constructed in any number of different ways. For example, a stainless steel rod 0.003" smaller in radius than the desired final radius may be coated with a layer of alumina approximately 0.010" thick. Subsequently, the rod may be machined to the desired radius, resulting in a layer of alumina of thickness 0.003". The alumina-coated rod would then be masked, and the resistive coating 330 applied. As resistive coating 330 can be very thin, perhaps having a thickness of 10 microns or less, the thickness of resistive coating 330 need not significantly affect the radial dimension of the rods. Finally, metal bands may be applied to each end of the rods 322 and 324 to facilitate good ohmic contact with lead wires from variable DC quadrupolar voltage sources 328a and 328b at one end, and with lead wires 329 at the other end.

Alternatively, and more simply, ordinary stainless steel rods 322 and 324, already machined to normal specifications, may be coated with a high-dielectric polymer (the resistive coating 330), which is sufficiently resistive such that a 10 micron layer suffices to withstand 100 Volts DC. Subsequently, ions are implanted in the polymer layer to a depth of only a few microns to create the resistive coating 330. As described above, metal bands at the ends insure good ohmic contact between the resistive coating 330 and, at one end, lead wires from variable DC quadrupolar voltage sources 328a and 328b, and, at the other end, lead wires 329.

A third method of making the rod set of FIG. 3 involves chemical vapour deposition (CVD) of an insulating layer from [2,2]-para-cyclophane paralyne to an average depth of 23 μm, followed by CVD of a resistive coating of hydrogenated amorphous silicon (a-Si:H) film of estimated thickness ~0.5 μm.

Figure 4:
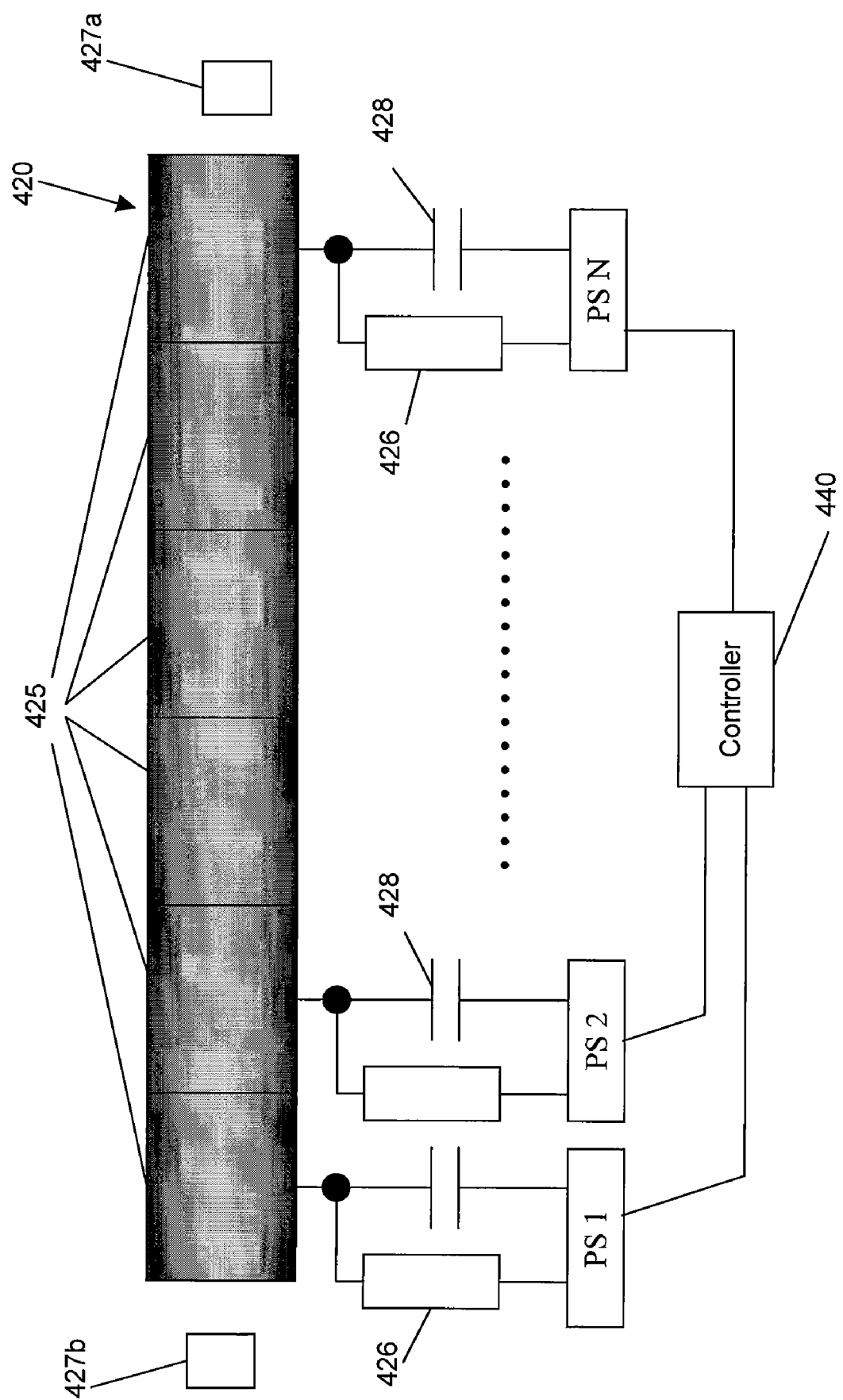
FIG. 4, in a schematic view, illustrates one rod of an ion guide in accordance with a third aspect of the present invention.

Referring to FIG. 4, there is illustrated in a schematic view, an ion guide 420 in accordance with a third aspect of the present invention. For brevity, the description of FIG. 3 is not repeated with respect to FIG. 4. For clarity, elements analogous to those described above in connection with FIG. 3 will be designated using the same reference numerals with 100 added.

The ion guide 420 is divided into a plurality of segments 425. The exit of the ion guide 420 is located on the right side of FIG. 4. An exit electrode 427a is provided at the exit end of the ion guide 420, while an entrance electrode 427b is provided at the entrance end. The same RF voltage can be applied to each segment of the ion guide to radially confine the ion beam. For each segment in the plurality of segments 425, an individual voltage—Ui for the $i_{th}$ segment for example—can be superimposed with the RF voltage. Each voltage Ui can be individually selected and can comprise quadrupolar DC component voltage, such that all of the quadrupolar DC voltages together can provide any desired profile along the axis of the ion guide 420. For example, as shown, individual voltages U1 and U2 are supplied to their respective segments by independently controllable power supplies PS1 and PS2.

Each individual power supply PSi comprises an associated resistor 426 and an associated capacitor 428, and is controlled by controller 440. The resistors 426 are primarily responsible for determining the particular quadrupolar DC voltage applied to their respective segments, while the capacitors 428 are predominantly responsible for determining the AC voltage provided to their respective segments. By this means, different DC and AC voltages may be applied to different segments of the ion guide 420. Thus, for example, the quadrupolar DC provided by PS1 to the first segment may slightly exceed the quadrupolar DC voltage supplied by PS2 to the second segment, which may, in turn, slightly exceed the DC quadrupolar voltage supplied by PS3 (not shown) to the third segment. By this means, the overall quadrupolar DC voltage profile provided may be represented by a step function, in which the quadrupolar DC voltage remains constant over each segment in the plurality of segments 425 of the ion guide 420, and then changes abruptly to a different quadrupolar DC voltage at a new segment. However, if the dimensions of each of the segments in the plurality of segments 425 along the axis of the ion guide are made as small as possible, then this step function can approach a straight line, such that differentiating with respect to the axial coordinate z can yield a force that approaches being axially uniform.

In general, the voltage Ui(t) applied to each individual segment can, as shown, be a function of time. Specifically, the quadrupolar DC component of Ui can be a function of time. Thus, for example, in both the first step, in which multiple precursor ions of interest are trapped and isolated, and the second step in which the selected precursor ion is excited using dipolar excitation, the same quadrupolar DC voltage can be applied to each segment in the plurality of segments 425 such that there is no derived axial force acting on any of the precursor ions. Then, in step 3, different quadrupolar DC voltages can be applied to each of the segments in the plurality of segments 425. The resulting quadrupolar DC voltage gradient creates a derived axial force that acts on the precursor ion that has been excited in step 2 and thereby displaced towards one of the rod pairs: the derived axial force pushes that exited ion towards the exit end. Then, in step 4, the same quadrupolar DC voltage is once again applied to all of the segments in the plurality of segments 425.

Figure 5:
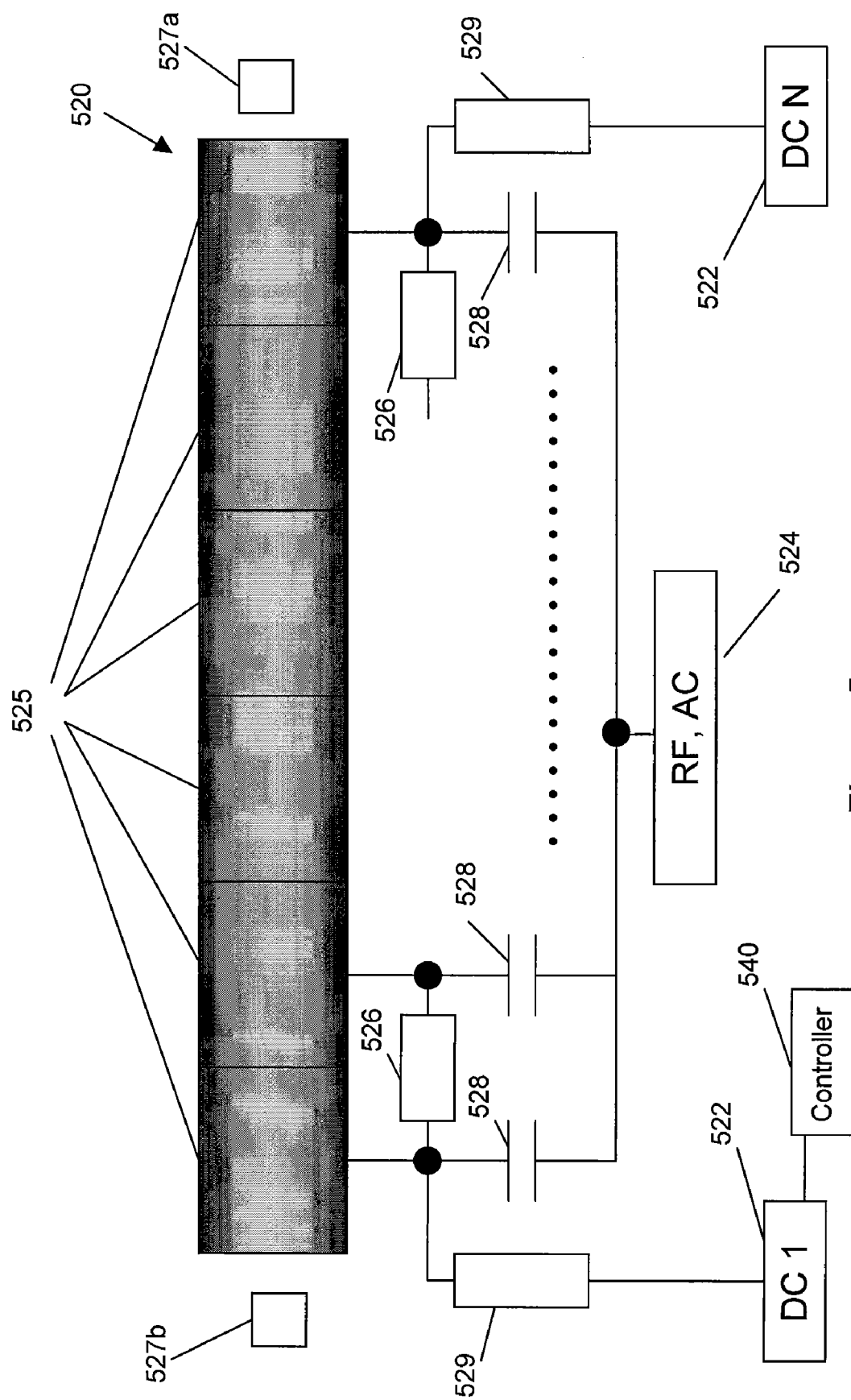
FIG. 5, in a schematic view, illustrates one rod of an ion guide in accordance with a fourth aspect of the present invention.

Referring to FIG. 5, there is illustrated in a schematic view, an ion guide 520 in accordance with a fourth aspect of the present invention. For clarity, the same reference numerals with 100 added are used to designate elements analogous to those described above in connection with FIG. 4. However, for brevity the description of FIG. 4 is not repeated with respect to FIG. 5.

The quadrupolar DC voltage profile applied to the ion guide 520 of FIG. 5 is determined by the power supply 522, end resistors 529 and inter-segment resistors 526. Power supply 522 is controlled by controller 540. The inter-segment resistors 526 are used to enable the quadrupolar DC voltage profile to be supplied by only the single DC power supply 522. The quadrupolar DC voltage profile varies between the plurality of segments 525 of the ion guide 520 based on the resistances of the inter-segment resistors 526. If all of the resistors have the same resistance, and all of the segments in the plurality of segments 525 have the same dimensions, then the quadrupolar DC voltage applied to the plurality of segments 525 changes uniformly from segment to segment along the length of the ion guide 520.

A single RF/AC voltage supply 524 provides RF/AC voltage to each of the segments in the plurality of segments 525 via capacitors 528. Assuming that each of the capacitors 528 has an appropriate capacitance, the same RF/AC voltage will be applied to each segment.

As described above, during the first few stages of operation, the quadrupolar DC voltage supply means 522 will not, in some embodiments, provide a quadrupolar DC voltage gradient along the length of the ion guide 520. In other words, in some embodiments no DC quadrupolar voltage gradient is provided along the length of the ion guide 520 while the multiple precursor ions of interests are being admitted to the entrance of the ion guide 520 and are being trapped by RF/AC voltage supply 525 providing an RF field to the rods to radially contain the ions, while suitable exit and entrance barrier voltages are provided to exit and entrance electrodes 527a and 527b respectively to axially contain the ions. As a result of the quadrupolar DC voltage along the length of the ion guide 520 being constant, no derived axial force acts on the trapped ions. Then, after a selected precursor group of ions, having selected m/z, has been excited, and thereby displaced toward one of the rod pairs, the quadrupolar DC voltage supply means 522 can be turned on to supply the quadrupolar DC voltage to the plurality of segments 525 of the ion guide 520. Due to the inter-segment resistors 526, the quadrupolar DC voltage applied varies from segment to segment, thereby creating the derived axial force that acts on the excited ions. After the excited ions have been sufficiently accelerated by this derived axial force, the DC voltage supply means 522 can once again be turned off such that the quadrupolar DC voltage is constant along the lengths of the ion guide 520. The exit barrier voltage S2 provided to exit electrode 527a can then be reduced to just above the DC voltage supplied to all of the rods so that the excited ions pass through the exit barrier while the unexcited ions are retained.

In the ion guide 520 of FIG. 5, the quadrupolar DC voltage profile varies between the plurality of segments 525 based on the resistance of the resistors 526. Thus, the shape of this voltage profile will typically be defined by the resistance of resistors 526. In some situations, however, it may be desirable to allow the quadrupolar DC voltage profile to be changed more readily.

Figure 6:
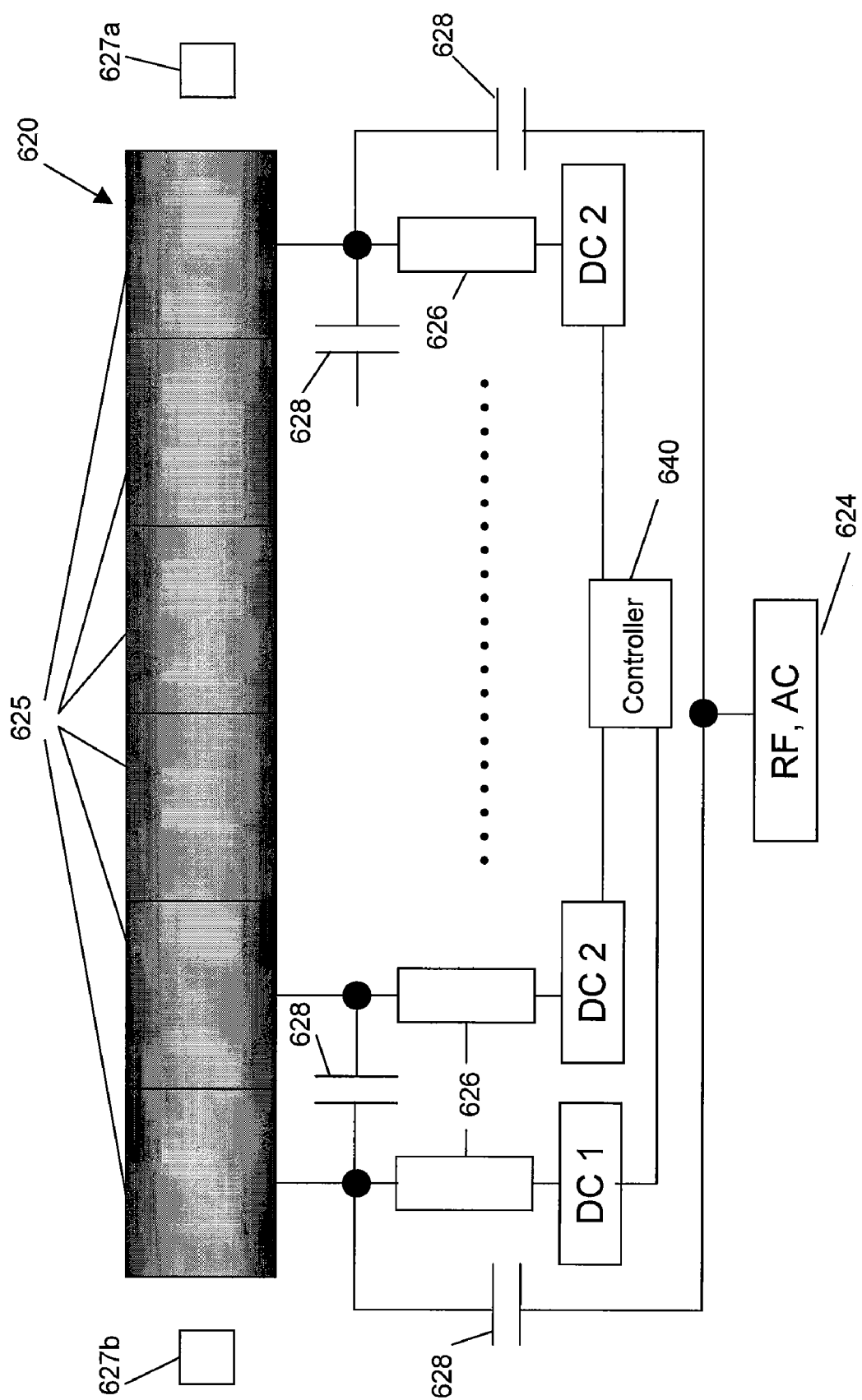
FIG. 6, in a schematic view, illustrates one rod of an ion guide in accordance with a fifth aspect of the present invention.

Referring to FIG. 6, there is illustrated in a schematic view, an ion guide 620 in accordance with a fifth aspect of the invention. For clarity, the same reference numerals, with 100 added, are used to designate elements analogous to those described above in connection with FIG. 5. However, for brevity, the description of FIG. 5 is not repeated with respect to FIG. 6.

In FIG. 6, a single RF/AC power supply 624 is linked via capacitors 628 to each segment in the plurality of segments 625 of the ion guide 620. In this case, the shape of the RF/AC voltage profile provided to the ion guide 620 is predetermined by the values of the capacitors 628, although, of course, the magnitude of these AC voltage profiles can be changed by AC power supply 624. In contrast, individual and independently controllable DC power supplies are provided for each segment in the plurality of segments 625. Each of the DC power supplies is controlled by controller 640. Each of these individual power supplies is connected to an associated segment by a resistor 626. In this case, the DC voltage profile provided along the ion guide 620 can be varied by independently controlling the individual DC power supplies for each of the segments.

While ion guide 620 of FIG. 6 allows the quadrupolar DC voltage profile to be more readily controlled than in the case of the ion guide 520 of FIG. 5, it achieves this at the cost of greater complexity. That is, it provides independent controllable DC power supplies for each segment in the plurality of segments 625. In contrast, the ion guide 520 of FIG. 5 requires but a single DC power supply 522 and a single RF/AC power supply 524.

Figure 7:
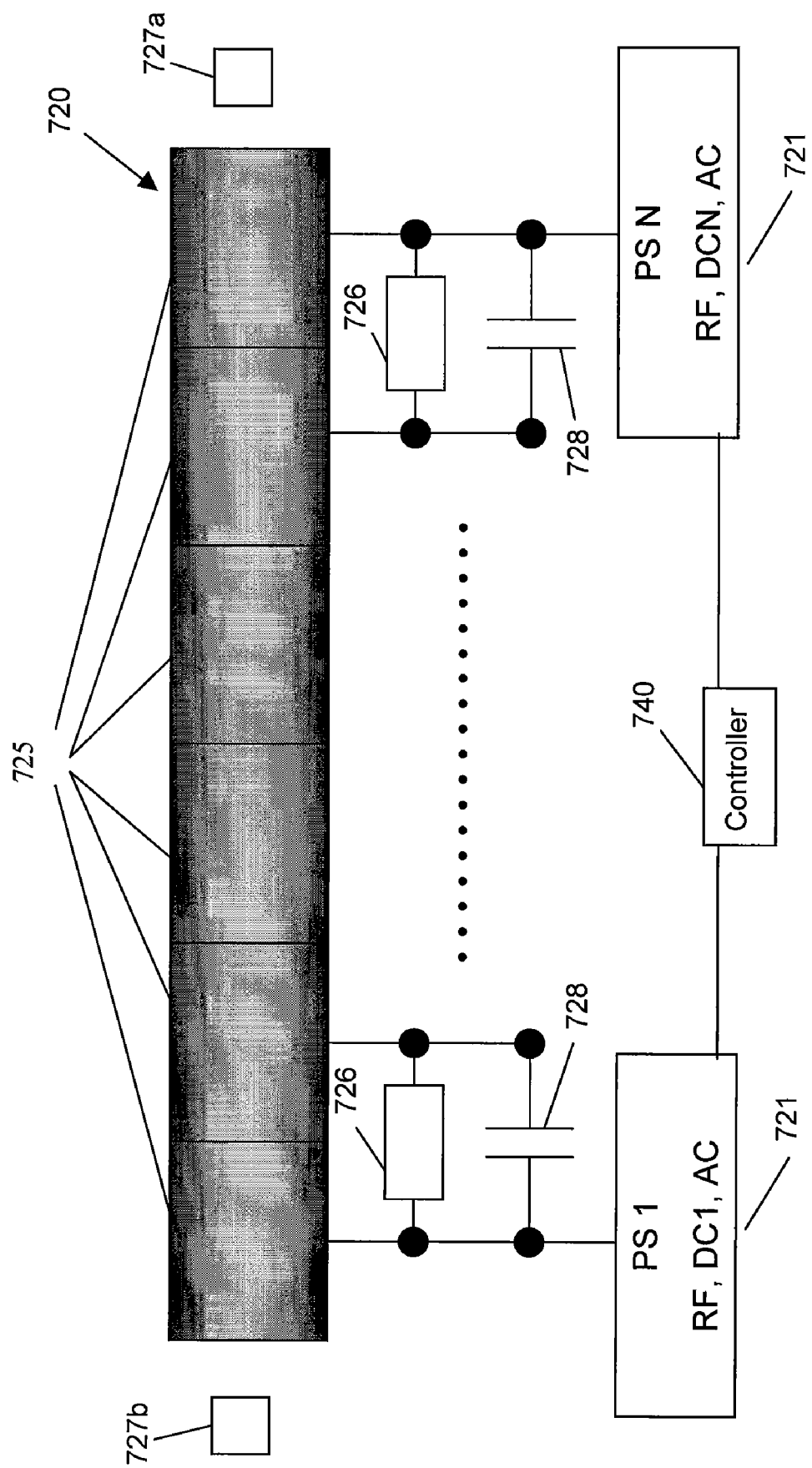
FIG. 7, in a schematic view, illustrates one rod of an ion guide in accordance with a sixth aspect of the present invention.

Referring to FIG. 7, there is illustrated in a schematic view, an ion guide 720 in accordance with a sixth aspect of the invention. For clarity, the same reference numerals, with 100 added, are used to designate elements analogous to those described above in connection with FIG. 6. However, for brevity, the description of FIG. 6 is not repeated with respect to FIG. 7.

The ion guide 720 of FIG. 7 comprises only a single power supply 721, which is responsible for providing the RF/AC voltage and quadrupolar DC voltage to each of the segments in the plurality of segments 725. That is, as shown in FIG. 7, power supply 721 is directly linked to the first and last segments in the plurality of segments 725. The intermediate segments between the first and last segments, are coupled along an RF path by capacitive dividers 728, and the RF voltage supplied by the power supply 721 is supplied to these individual segments via these capacitive dividers 728. The capacitances of these capacitive dividers 728 define the RF voltage profile along the length of the ion guide 720. Ideally, the capacitances of the capacitive dividers 728 are chosen to be sufficiently large such that the RF voltage will not drop appreciably over the length of the rods. However, in some applications, it may be desirable to vary the magnitude of quadrupolar RF along the length of the rods by increasing or varying the capacitances of the capacitive dividers 728.

Quadrupolar DC voltage is directly provided to the first and last segments by the power supply means 721. The intermediate segments between the first and last segments are coupled along a DC path by resistors 726 and the DC voltage supplied by the power supply 721 is supplied to the individual segments via these resistors 726. The resistances of resistors 726 define the quadrupolar DC voltage profile along the length of the ion guide 720. As described above in connection with FIG. 5, a uniform quadrupolar DC profile can be provided along the length of the ion guide 720 by simply making the quadrupolar DC voltage supplied equal to zero Volts.

Although in FIG. 7, as well as in FIGS. 3 to 6, the DC and RF paths are shown intersecting, it will be appreciated by those of skill in the art that these paths, should, in fact, be isolated from each other.

Figure 8:
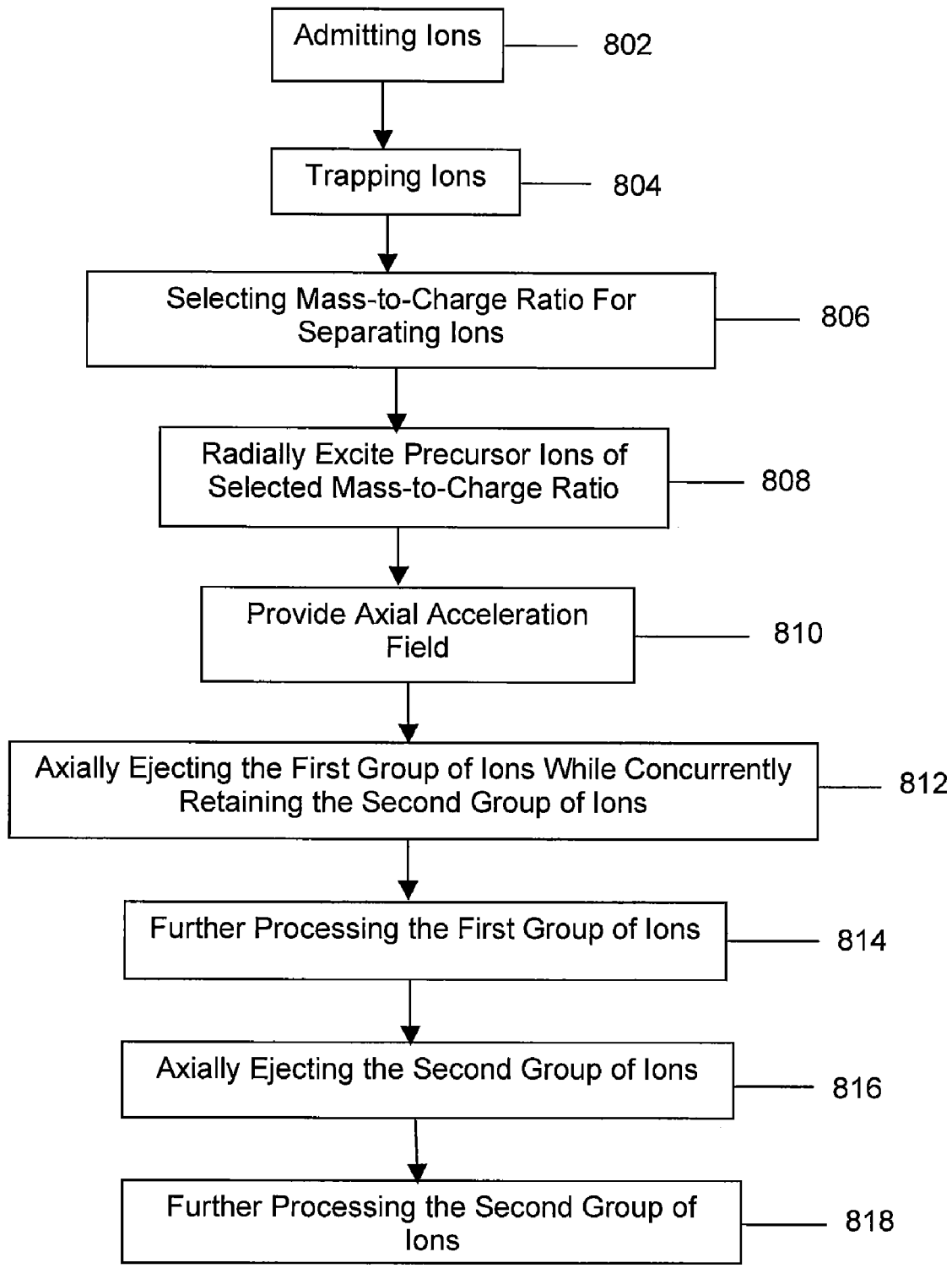
FIG. 8, in a flow chart, illustrates a method of providing a pulsed axial acceleration field to sequentially and axially eject selected groups of ions in accordance with a seventh aspect of the present invention.

Referring to FIG. 8, there is illustrated in a flowchart a method of separating ions in accordance with an aspect of the present invention. In step 802 of the flowchart of FIG. 8, ions are admitted into the entrance end of the rod set. Then, in step 804, the ions are trapped in the rod set by producing an exit field at the exit electrode of the rod set adjacent to the exit end of the rod set, and by producing an RF field between the rods of the rod set to radially confine the ions in the rod set. Step 804 can also include collisional cooling and focusing that are commonly accomplished by providing sufficient pressure of a buffer gas in the trap region. In step 806, a mass-to-charge ratio for separating the ions into at least two different groups of ions is selected. Typically, the mass-to-charge ratio selected will be the lowest mass-to-charge ratio among the precursor ions. In step 808 the selected precursor ions are excited in the radial dimension using an excitation voltage as described above. The excitation field can have a dipolar component, a quadrupolar component or any other suitable components and their superpositions. According to some aspects of the invention, during each of steps 802, 804, 806 and 808, no or very little quadrupolar DC voltage gradient is provided to the rod set, such that no quadrupolar DC component field, in particular, or axial acceleration field, in general, is provided.

Then, in step 810 an axial acceleration field is provided. In some embodiments, the dipole excitation field is turned off before this axial acceleration field is provided. Also, in some embodiments the axial acceleration field is provided by providing a quadrupolar DC voltage gradient to the rod set, which quadrupolar DC voltage gradient gives rise to a derived axial force.

When the dipole excitation field was provided in step 808, the ions within the rod set were divided between a first group of ions, which were moved radially outward away from the central axis of the rod set, and a second group of ions that were not excited and thus remained grouped around the central axis. In step 810, the axial acceleration field or derived axial force acts on the first group of ions to a much greater extent than the second group of ions, accelerating this first group of ions toward the exit end of the rod set.

In step 812, the exit barrier voltage is lowered sufficiently to allow the first group of ions, which have been accelerated towards the exit end of the rod set in step 810, to pass through the exit barrier, while being kept strong enough to concurrently retain the second group of ions. In step 814, the first group of ions, after axial ejection, can be further processed. This may be merely by detection, or, alternatively, may involve further processing steps, such as, for example, fragmentation. Subsequently, in step 816, the second group of ions may be axially ejected for further processing in step 818. This axial ejection of the second group of ions would proceed in substantially the same way as that employed for the first group of ions. That is, first the second group of ions would be excited using a dipolar excitement voltage as described above, and by changing the RF amplitude of the RF field so as to bring the second group of ions into resonance with the dipolar excitement voltage. Again, as described above, in some aspects of the invention, no or little quadrupolar DC voltage gradient would be provided to the rod set while this second group of ions is being excited. Subsequently, an axial acceleration field can be provided to push the second group of ions toward the exit barrier. As in step 812, the exit barrier voltage can then be lowered sufficiently to allow the second group of ions to pass through the exit barrier, while retaining any other non-accelerated ions. Additional groups of ions of different m/z can subsequently be ejected in an analogous manner.

Figure 9:
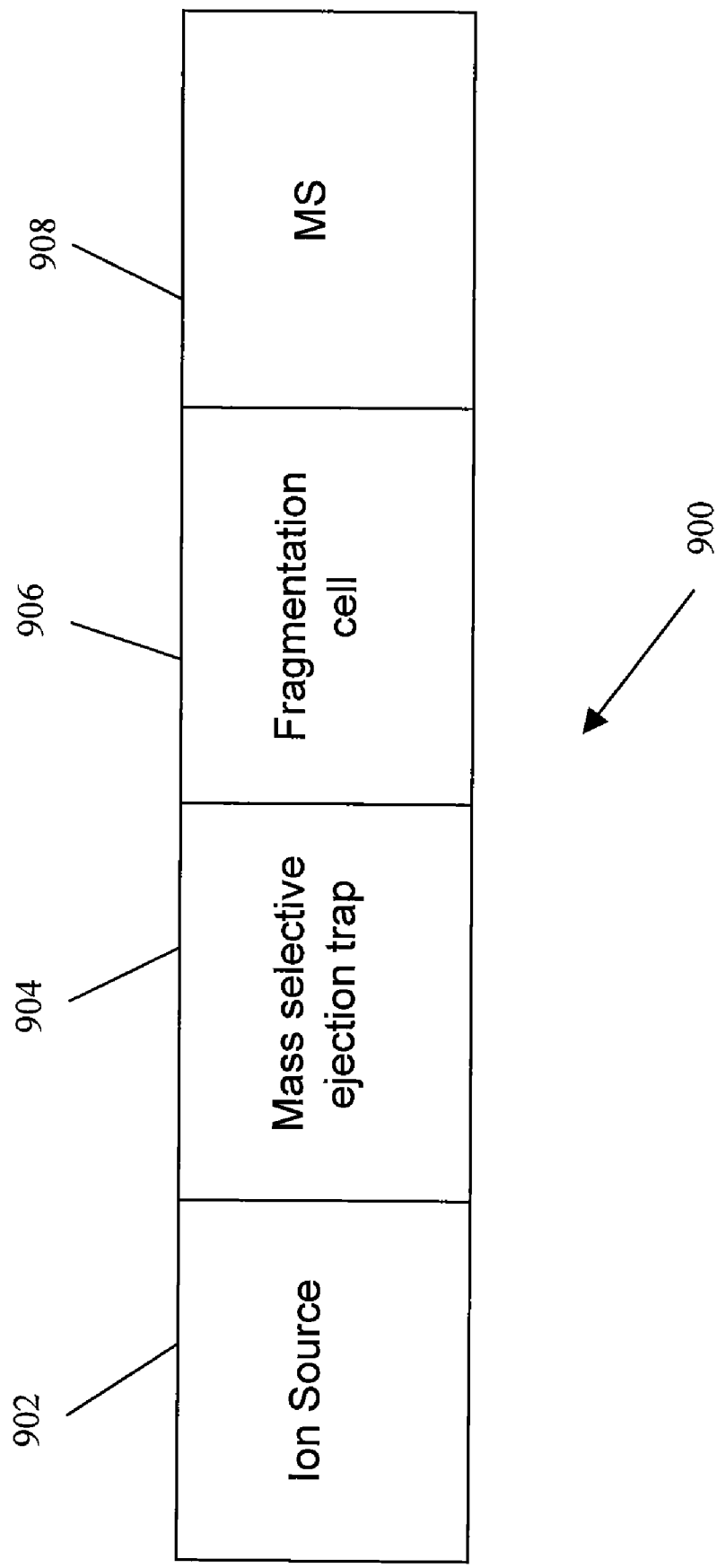
FIG. 9, in a block diagram, illustrates an MS/MS arrangement in accordance with an eighth aspect of the present invention.

Referring to FIG. 9, there is illustrated in a block diagram, a tandem mass spectrometer arrangement 900 in accordance with a yet further aspect of the invention. The tandem mass spectrometer arrangement 900 includes an ion source 902, which emits ions into a mass selective ejection trap 904, such as the ion guides of any of FIGS. 3 to 7. The ion source 902 can be any suitable ion source. For example, an electro-spray ionization (ESI) source or a matrix assisted laser desorption/ionization (MALDI) source or an electron impact (EI) source. The ion source can provide a continuous stream of ions or a pulsed stream of ions. As described above in connection with FIG. 8, the ions are trapped in the mass selective ejection trap 904. One convenient mode of operation is when the ion source generates a pulsed stream of ions and the pulses are synchronized with the axial ejection trap operating cycle. In this case, the ions generated by the ion source can be accumulated in the axial ejection trap and processed. On the other hand, if the ion source generates a continuous ion stream or an unsynchronized pulsed ion stream the trap can be open for a certain duration allowing ions to accumulate and then closed preventing further ions from coming in during further steps of processing. To avoid losses of the incoming ions during processing steps, an additional accumulation ion trap can be placed upstream of the axial ejection trap. The accumulation trap can continue to accumulate ions even when the axial ejection trap is closed. Accumulated ions will then be sent to the axial ejection trap when it is ready to receive the ions. The duration of the ion accumulation interval and the ion beam intensity control the number of ions collected in the trap. This number should be kept below a certain limit to avoid the influence of space charge effects on the operation of the trap. The limit is often referred to as space charge capacity of the trap. Therefore, if the beam intensity is high it may be necessary to admit only a fraction of ions while rejecting the rest of them to keep the number of ions within the space charge capacity limit. In such a situation one method to improve utilization of the ions is to filter the ion stream and retain only the ions of interest. Then, the space charge capacity is not wasted to store the ions that are of no interest. This can be accomplished, for example, by applying filtered noise filter (FNF) or simulated waveform inverse Fourier transform (SWIFT) technique during the accumulation step. If the ions from the ion source go directly to the axial ejection trap, then appropriate electronics to apply the filtering during accumulation can be connected to the axial ejection trap. In the case when the accumulation trap is used prior to the axial ejection trap it is more advantageous to filter the ions in the accumulation trap and the corresponding filtering electronics should be attached to the accumulation trap.

Once the trap 904 is filled, a particular group of ions, of a selected mass-to-charge ratio, are selected. Again, as described above in connection with FIG. 8, this group of ions is first subjected to a dipole excitement field to move them radially away from the central axis. Other ions of different m/z, are concurrently retained closer to the central axis. Then, a quadrupolar DC voltage gradient is provided to the rod set, which, in turn, gives rise to a derived axial force, which pushes the excited group of ions toward the exit end of the mass selective ejection trap 904. Sufficient momentum is provided to this selected group of ions to enable them to pass through the barrier at the exit of the mass selective ejection trap 904 and from thence into the fragmentation cell 906. In fragmentation cell 906, the selected group of ions can be fragmented and then axially ejected and subjected to detection in mass spectrometer 908. Subsequent to the ejection of the fragments of the first selected group of ions from the fragmentation cell 906, a second selected group of ions can be axially ejected from the mass selective trap 904, in the same manner as that described above with respect to the first selected group of ions, to the fragmentation cell 906, for subsequent fragmentation and downstream detection by mass spectrometer 908.

Figure 10:
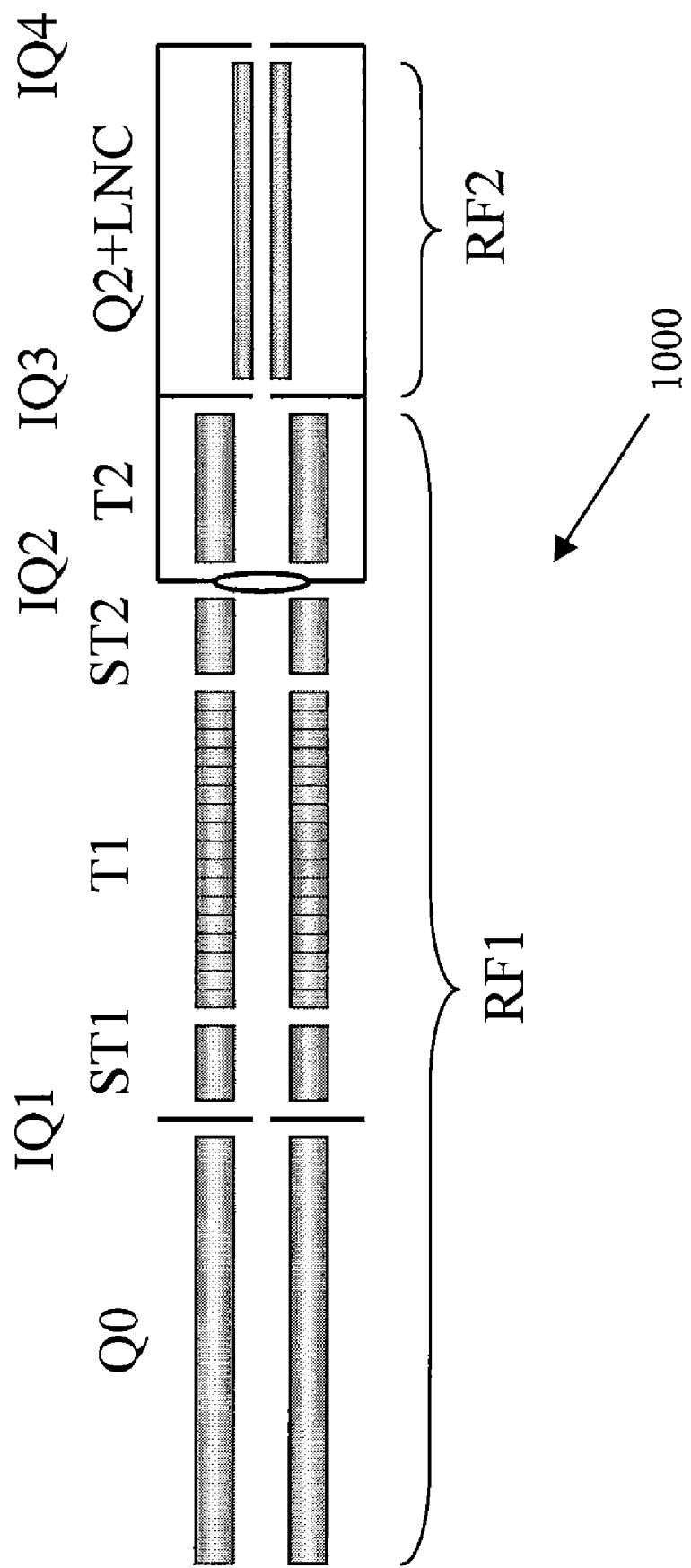
FIG. 10, in a schematic view, illustrates a second MS/MS arrangement in accordance with a ninth aspect of the present invention; and, FIG. 11, in a schematic view, illustrates a third MS/MS arrangement in accordance with a tenth aspect of the present invention.

Referring to FIG. 10, there is illustrated in a schematic diagram, a linear ion trap mass spectrometer system 1000 in accordance with a ninth aspect of the invention. The mass spectrometer system 1000 comprises four elongated sets of rods; Q0, T1, T2 and Q2, with orifice plates IQ1 after rod set Q0, IQ2, before rod set T2, IQ3 between rod sets T2 and Q2 and IQ4 after rod set Q2. Additional sets of stubby rods ST1 and ST2 are provided between orifice plate IQ1 and rod set T1, and between rod set T1 and orifice plate IQ2 respectively. In accordance with different aspects of the invention, rod set T1 may be any of the rod sets of FIGS. 3 to 7 or any other rod set suitable for implementing the mass selective axial transport of the method of FIG. 8.

Ions from the ion source may be, and in some embodiments are, cooled in Q0, which may be, and in some embodiments is, maintained at a pressure of approximately $8 \times 10^{-2}$ Torr. Stubby rods ST1 are provided between orifice plate IQ1 and rod set T1 to focus the flow of ions into rod set T1. In some embodiments, T1 may have a length of 10 cm, with a space charge capacity of approximately two million singly charged ions. The pressure in T1 can be maintained at $3 \times 10^{-5}$ Torr. In some embodiments, T1 can operate at a cooling and isolation interval of 100 ms and a mass selective ejection cycle of 5 ms per cycle per precursor. For example, at a cycle of 100 ms if 20 precursors are chosen. In some embodiments, T1 may have an operating rate of 5 Hz assuming 20 precursor ions, and the maximum average ion current out of Q2 would be approximately 10 Mions/sec.

Within rod set T1, the precursor ions of interests can be, and in some embodiments are, isolated using notched FNF or SWIFT excitations. Alternatively, quadrupolar RF and DC filtering, or a combination of both, or any other suitable method may be used to isolate the precursor ions of interest. Subsequently, the ions can be, and in some embodiments are, axially ejected from T1, through ST2, IQ2, T2 and IQ3 to Q2. IQ2 has a large elliptical orifice to accommodate the ion beam from T1. T2 can be used for collisional dampening of radial energy of the excited ions. In addition, it can provide a convenient way to achieve higher energies for CID. Once the ions are trapped in T2 the offset voltage of T2 can be increased to a desired level. Ions stored in T2 will remain in it until the exit barrier (IQ3) is lowered and the ions exit into collision cell. The axial velocity of ions will be determined by the potential difference between T2 and Q2. Since T2 operates at high RF voltage it can readily tolerate high offset voltage. The offset voltage of Q2 on the other hand can be limited due to constraints on the following stages of the mass spectrometer. For example, if Q2 is coupled to an orthogonal injection Time-of-Flight (TOF) instrument the Q2 offset voltage can be fixed and linked to the other parameters of TOF mass analyzer. Alternatively, the T2 offset voltage can be kept at a fixed potential while Q2 offset voltage is lowered to obtain the desired collision energy. Trapping barrier (IQ4) can be used to prevent ions from leaving Q2. Once the ions fragment and settle down the offset of Q2 can be brought to the desired level. Only then the IQ4 barrier can be opened to allow ions to proceed to the following stages of the instrument starting at the desired Q2 offset potential. These modes of operation are useful when a higher level of axial energy is required for CID, for example for high mass ions generated by (MALDI).

Therefore, a sufficient potential difference between T1 and Q2 can be provided to ensure CID fragmentation of the precursor ions. Alternatively, other means of modification of precursor ions, such as photo-fragmentation, ion/neutral bombardment, electron capture/transfer dissociation or ion reactions and so on may be used. Once the ions are within Q2, they can be further analyzed by any suitable mass analyzer.

Subsequently, the fragment ions can be accumulated in Q2 and sent back to T1. Once the fragment ions are within T1, fragment ions of different kinds can be selectively ejected using a radial excitement field and a pulsed axial acceleration field in the manner described above and axially ejected back to Q2 for further fragmentation. Then, they can be further analyzed to obtain a fragmentation mass spectrum recording for every fragment of the ion of interest. Subsequently, a second fragment ion of interest can be axially ejected from T1 using a radial excitement field and a pulsed axial acceleration field as described above.

Through this means, a collection of fragmentation mass spectra of fragments can be obtained, instead of only one fragment being isolated and fragmented in a particular operation. In addition, in an apparatus comprising additional mass spectrometers, further fragmentation steps could be taken to increase the information obtainable from a single run. In another mode of operation, precursor ions of interest are isolated in T1 and then sent directly to Q2 for fragmentation. Once the fragments are collected in Q2 they can be returned to T1 and then sequentially processed according to the method of FIG. 8. Thus, a set of fragmentation mass spectra of the fragment ions will be collected providing information that is often referred to as $MS^3$.

Figure 11:
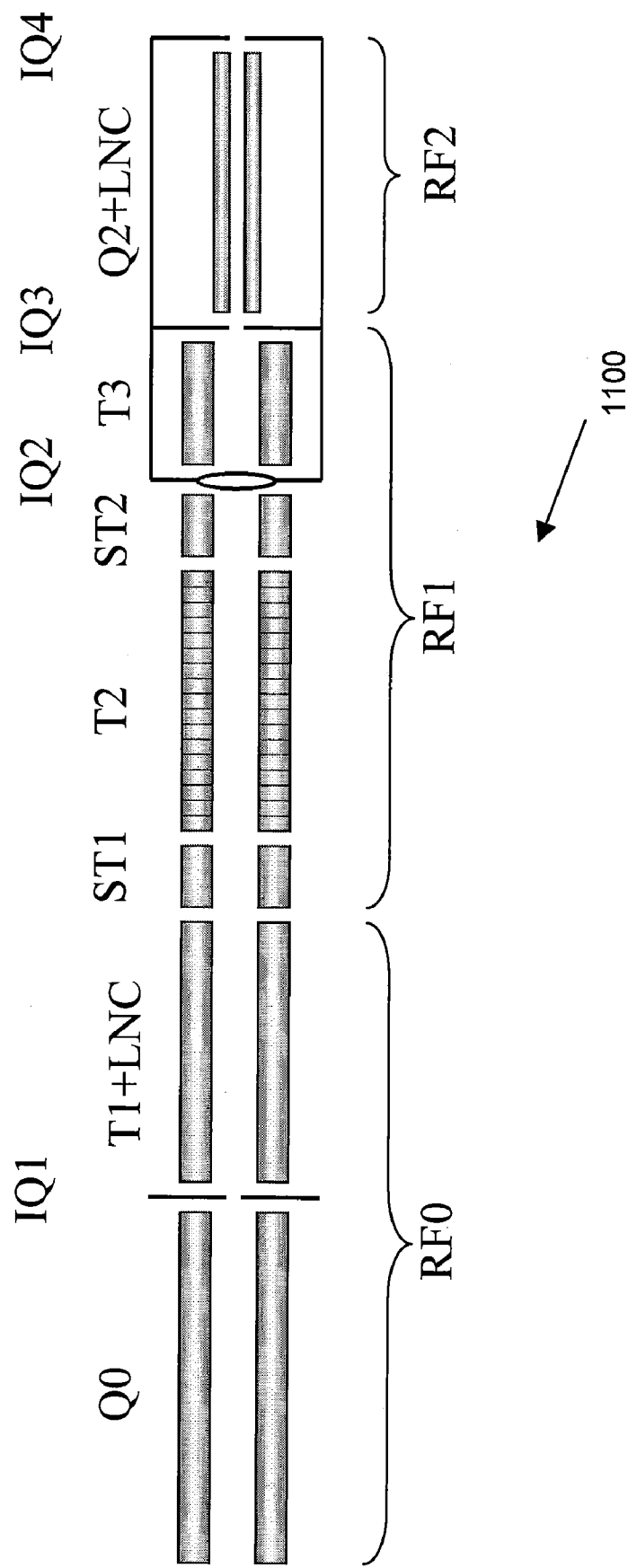

Referring to FIG. 11, there is illustrated in a schematic diagram, a linear ion trap mass spectrometer system 1100 in accordance with a tenth aspect of the present invention. For brevity, the description of FIG. 10 is not repeated with respect to FIG. 11.

The linear ion trap mass spectrometer system 1100 of FIG. 11 is similar to the linear ion trap mass spectrometer 1000 of FIG. 10. However, the linear ion trap mass spectrometer system 1100 includes an additional elongated rod set T3, which takes the place of T2 in the linear ion trap mass spectrometer system 1000. T2 of mass spectrometer system 1100 is analogous to T1 of the mass spectrometer system 1000 (FIG. 10). In linear ion trap mass spectrometer system 1100, multiple precursor ions can be isolated in T1. Different RF voltages can then be independently applied to T1 and T2, to store and isolate precursor ions in T1 while T2 is mass selectively ejecting another portion of ions. This setup is particularly useful when working with a high intensity continuous ion beam as it can get around duty cycle losses in the axial ejection trap. Indeed, when the ions are mass selectively ejected from T1 shown in FIG. 10, the entrance to T1 can be blocked and ions can be accumulate in Q0. But, if the ion flux is high the ions quickly overfill space charge capacity of Q0. In contrast, the setup shown in FIG. 11 can allow continuous accumulation and isolation of ions of interest in T1. Since the ions in T1 can be isolated (i.e. unwanted ions can be removed) the rate of space charge accumulation can be reduced; therefore T1 can accumulate the ions for a longer period of time sufficient to process all the ions of interest in T2. By this means, the mass spectrometer system 1100 of FIG. 11 can be used to process a continuous ion beam while reducing losses of ions of interest.

Other variations and modifications of the invention are possible. For example, instead of a quadrupolar DC component field being provided, other suitable means may be employed to provide an axial acceleration field, which exerts a force on ions relative to their displacement from the central axis of the mass spectrometer. For example, auxiliary electrodes can be added to the rod set. These electrodes can be sloped (see Loboda A, Krutchinsky A., Loboda O., McNabb J., Spicer V., Ens W., Standing K. G. Eur. J. Mass Spectrom. 2000; 6: 531) to create an axial field. By applying voltages of opposite polarities to the opposite pairs of these electrodes the axial field can be kept at zero near the axis. At the same time since the axial field is non-zero away from the axis excited ions will be subjected to the net axial acceleration. In another embodiment an axial field produced by the main rod set is counteracted by the axial filed produced by the auxiliary electrodes such that the axial field in the center of the rod set is kept at zero while the axial field away from the center of the rod set is non-zero and therefore can accelerate a group of ions that have high amplitude or radial oscillations. All such modifications or variations are believed to be within the sphere and scope of the invention as defined by the claims appended hereto.

This invention claimed is:

1. A method of operating a mass spectrometer system having an elongated rod set, the rod set having an entrance end, an exit end, a plurality of rods and a central longitudinal axis, the method comprising:
   a) admitting a first plurality of groups of ions into the entrance end of the rod set;
   b) producing a field between the plurality of rods to confine the first plurality of groups of ions in the rod set;
   c) selecting a first mass/charge range for a first group of ions in the first plurality of groups of ions;
   d) providing a first radial excitement field to radially displace the first group of ions within the first mass/charge range from the central longitudinal axis, and concurrently retaining a second group of ions closer to the central longitudinal axis than the first group of ions, the second group of ions being within a second mass/charge range disjoint from the first mass/charge range; and then
   e) providing a first axial force acting on the first group of ions by providing an axial acceleration field;
   wherein the first axial force is not provided during step d).

2. The method as defined in claim 1 wherein steps d) and e) occur at different times such that the first radial excitement field is not provided during step e).

3. The method as defined in claim 1 wherein step d) comprises applying a first dipolar, auxiliary signal to a rod pair in the rod set and selecting a first RF amplitude of the RF field to bring the first group of ions into resonance with the first dipolar, auxiliary signal to move the first group of ions in the radial direction toward the rod pair.

4. The method as defined in claim 1 wherein
   the plurality of rods comprises a first set of rods and a second set of rods, and step (e) comprises providing the axial acceleration field by providing a first DC voltage to the first set of rods and a second DC voltage to the second set of rods, the first DC voltage being opposite in polarity to the second DC voltage; and,
   the axial acceleration field varies along at least a portion of a length of the rod set to provide the first axial force acting on the first group of ions.

5. The method as defined in claim 4 wherein
   step b) comprises providing an exit barrier field at the exit end of the rod set to impede axial ejection of the second group of ions from the exit end; and,
   step e) comprises providing sufficient momentum to the first group of ions to push the first group of ions past the exit barrier.

6. The method as defined in claim 4 wherein the mass spectrometer system further comprises an upstream ion trap for isolating the first plurality of groups of ions in step (a), and step (a) further comprises ejecting the first plurality of groups of ions from the upstream ion trap to admit the first plurality of groups of ions into the entrance end of the rod set.

7. The method as defined in claim 4 wherein step (b) comprises
   providing an RF field between the plurality of rods to radially confine the first plurality of groups of ions in the rod set; and,
   providing an exit barrier field at the exit end of the rod set and an entrance barrier field at the entrance end of the rod set to axially confine the first plurality of groups of ions in the rod set.

8. The method as defined in claim 5 further comprising
   f) after pushing the first group of ions past the exit barrier, providing a second radial excitement field to radially displace the second group of ions within the second mass/charge range from the central longitudinal axis, and concurrently retaining a third group of ions closer to the central longitudinal axis than the second group of ions, the third group of ions being within a third mass/charge range disjoint from the first mass/charge range and the second mass/charge range; and then
   g) providing the axial acceleration field to provide a second axial force acting on the second group of ions to provide sufficient momentum to the second group of ions to push the second group of ions past the exit barrier;
   wherein the second axial force is not provided during step f).

9. The method as defined in claim 5 wherein the method further comprises
   reducing the exit barrier after step (e) to facilitate axial ejection of the first group of ions;
   increasing the exit barrier after axial ejection of the first group of ions;
   reducing the exit barrier after step (g) to facilitate axial ejection of the second group of ions; and,
   increasing the exit barrier after axial ejection of the second group of ions.

10. The method as defined in claim 8 wherein
    steps d) and e) occur at different times such that the first radial excitement field is not provided during step e); and,
    steps f) and g) occur at different times such that the second radial excitement field is not provided during step g).

11. The method as defined in claim 10 wherein the first axial force and the second axial force increase with radial displacement from the central longitudinal axis.

12. The method as defined in claim 10 further comprising,
    before step a), isolating a first precursor group of ions from an ion sample, and then fragmenting the first precursor group of ions to provide the first plurality of groups of ions;

after pushing the first group of ions past the exit barrier in step e), detecting the first group of ions; and, after pushing the second group of ions past the exit barrier in step g), detecting the second group of ions.

13. The method as defined in claim 6 further comprising isolating a second plurality of groups of ions in the upstream ion trap after ejecting the first plurality of groups of ions from the upstream ion trap.

14. The method as defined in claim 13 wherein the mass spectrometer system further comprises one of i) an electrospray ionization module and ii) a high mass matrix assisted laser desorption/ionization module for providing gas phase ions to the upstream ion trap for subsequent isolation of the first plurality of groups of ions and the second plurality of groups of ions.

15. A mass spectrometer system comprising:
 a) an ion source;
 b) a rod set, the rod set having a plurality of rods extending along a longitudinal axis, an entrance end for admitting ions from the ion source, and an exit end for ejecting ions traversing the longitudinal axis of the rod set;
 c) a voltage supply module for producing an RF field between the plurality of rods of the rod set; and,
 d) a controller for controlling the voltage supply module to provide a radial excitement field to, i) during an excitation phase of operation, radially displace a first group of ions within a selected mass/charge range from the central longitudinal axis, and concurrently retain a second group of ions closer to the central longitudinal axis than the first group of ions, the second group of ions being within a second mass/charge range disjoint from the selected mass/charge range; and then ii) during an axial acceleration phase of operation, provided an axial force acting on the first group of ions by providing an axial acceleration field;
 wherein the controller is further operable to control the voltage supply module to interrupt the axial acceleration field during the excitation phase of operation such that the derived axial force is not provided during the excitation phase of operation.

16. The mass spectrometer system as defined in claim 15 wherein during the axial acceleration phase of operation the controller is operable to control the voltage supply module to add a quadrupolar DC component field to the RF field produced between the plurality of rods of the rod set.

17. The mass spectrometer system as defined in claim 15 wherein the controller is further operable to control the voltage supply module to interrupt the radial excitement field during the axial acceleration phase of operation.

18. The mass spectrometer system as defined in claim 15 wherein the controller is operable to provide the radial excitement field by controlling the voltage supply module to apply i) a selected dipolar, auxiliary signal to a rod pair in the rod set having the same polarity as the first group of ions and ii) a selected RF amplitude of the RF field to bring the first group of ions into resonance with the selected dipolar, auxiliary signal to move the first group of ions in the radial direction toward the rod pair.

19. The mass spectrometer system as defined in claim 18 wherein the controller comprises a user-input sub-module for receiving the selected mass/charge range from a user, the controller being operable to determine the selected RF amplitude of the RF field based on the selected mass/charge range.

20. The mass spectrometer system as defined in claim 15 the controller is further operable to control the voltage supply module to
 provide an exit barrier field at the exit end of the rod set to impede axial ejection of the second group of ions from the exit end; and,
 provide sufficient momentum to the first group of ions to push the first group of ions past the exit barrier.

21. The mass spectrometer system as defined in claim 20 the controller is further operable to control the voltage supply module to
 reduce the exit barrier after the axial acceleration phase of operation to facilitate axial ejection of the first group of ions; and
 increase the exit barrier after axial ejection of the first group of ions to retain the second group of ions.

22. The mass spectrometer system as defined in claim 15 wherein the first axial force and the second axial force increase with radial displacement from the central longitudinal axis.

* * * * *